United States Patent [19]

Borden et al.

[11] Patent Number: 5,418,192
[45] Date of Patent: May 23, 1995

[54] PRODUCTION OF IFN USING DA15 PEPTIDE

[75] Inventors: Ernest C. Borden, Madison, Wis.;
Michael Recht, New Haven, Conn.;
Ernest Knight, Jr., Wilmington, Del.

[73] Assignee: Medical College of Wisconsin Research Foundation, Milwaukee, Wis.

[21] Appl. No.: 998,896

[22] Filed: Dec. 28, 1992

Related U.S. Application Data

[63] Continuation of Ser. No. 590,565, Sep. 28, 1990, abandoned, which is a continuation-in-part of Ser. No. 486,473, Feb. 28, 1990, abandoned.

[51] Int. Cl.$^6$ .................. C12N 15/00; C12P 21/06; C12P 21/02; C07H 17/00
[52] U.S. Cl. .................. 435/69.51; 435/70.1; 435/172.3; 536/23.1
[58] Field of Search ............. 435/69.51, 70.1, 172.3; 536/23.1

[56] References Cited

PUBLICATIONS

"Differentiation Antigens in the Hematopietic System" by Immunotech.
G. Antonelli et al. "Generation of a Soluble IFN-Gamma Inducer by Oxidation of Galactose Residues on Macrophages" Cell. Immun. 94: 440-446 (1985).
N. Feltham et al., 9 J. Interf. Res. 493-507 (1989).
J. Carlin et al., 9 J. IFN Res. 167 et seq. (1989) (IDO activity).
J. Carlin et al., 139 J. Immunol. 2414-2418 (1987) (IDO induction).
J. Carlin et al., 9 J. IFN Res. 329 et seq. (1989) (IDO activity).
R. Devos et al., 10 Nuc. Acids Res. 2487-2501 (1982) (human interferon-gamma sequence information).
J. Vilcek, The Importance Of Having Gamma, in *Interferon* 1982, vol. 4, pp. 129-154 Academic Press (1982) (interferon-gamma).
Y. Ozaki et al. 144 Biochem. Biophys. Res. Commun. 1147-1153 (1987) (IDO tests).
M. Julius et al., 3 Eur. J. Immunol. 645-649 (1973) (nylon separation).
M. Edelstein et al., 143 J. Immunol. 2969-2973 (1989) (IDO induction by interferon-gamma).
B. Korant et al., 259 J. Bio. Chem. 14835-14839 (1984).
D. Blomstrom et al., 261 J. Bio. Chem. 8811-8816 (1986).
N. Reich et al., 84 P.N.A.S. USA 6394-6398 (1987).
A. Haas et al., 262 J. Biol. Chem. 11315-11323 (1987).
E. Knight et al., 263 J. Bio. Chem. 4520-4522 (1988).
E. Knight, Jr. et al., 8 J. Interf. Res. Supp. 1, S4 (1988).

*Primary Examiner*—David L. Lacey
*Assistant Examiner*—T. Michael Nisbet
*Attorney, Agent, or Firm*—Quarles & Brady

[57] ABSTRACT

An in vitro method for the production of interferon is set forth. The method involves the culture of monocytes with a new DA15 peptide produced in Daudi cell lines in response to stimulation with interferon gamma.

1 Claim, 12 Drawing Sheets

PRODUCTION OF IFN USING DA15 PEPTIDE

This invention was made with United States government support awarded by the National Institute of Health (NIH), Grant #P30 California 14520. The United States Government has certain rights in this invention.

This application is a continuation of application Ser. No. 07/590,565, filed Sep. 28, 1990, now abandoned. Apr. 7, 1994, which is a continuation in part of Ser. No. 07/486,473, filed Feb. 28, 1990, now abandoned.

This invention relates to the uses of an interferon induced protein to stimulate host defense mechanisms that rely on phagocytes.

BACKGROUND OF THE INVENTION

Phagocytes are blood cells that ingest and destroy other cells, microorganisms, and other foreign matter in the blood and tissues of animals. Monocyte/macrophages are phagocytes. Monocytes are immature cells that are produced in bone marrow and migrate into tissues and body cavities where they mature into macrophages. The monocyte/macrophage system plays a vital role in host defense mechanisms such as initiating and regulating immune responses; phagocytosing and killing microorganisms; exerting anti-tumor activities; phagocytosing and degrading effete cells, cellular debris, and other particulate matter; and secreting soluble biologically active substances. Given these functions, there has been considerable interest in finding substances that affect monocyte/macrophage activity.

In other unrelated work, there has been considerable research with respect to a group of proteins known as interferons. See generally E. Borden, 54 Cancer 2770–2776 (1984); E. Borden, *Interferons And Cancer: How The Promise Is Being Kept*, "Interferons", Vol. 5, Acad. Press 43–83 (1984). The disclosure of the above articles and of all other articles referred to herein are incorporated by reference as if fully set forth herein.

As a result of a large body research on the interferons, it has become clear that they induce the synthesis of many new proteins within cells they contact. It is also believed that some of the many proteins induced by the interferons must somehow mediate the interferon induced biological effects. However, the induced proteins' role in mediating the effects of interferons is unknown. See E. De Maeyer et al., "Interferons And Other Regulatory Cytokines", John Wiley And Sons (1988).

One interferon induced protein ("DA15") of about 15,000 daltons (about 156 amino acids) was isolated from the cytoplasm of a line of human lymphoblastoid cells after induction by interferon. Since then there have been reports on the purification to homogeneity of the protein, the isolation and location of the nucleotide sequence responsible for the protein, the amino acid sequence deduced from the cDNA therefor, particular portions of the gene responsible for transcription of the gene, and the mechanism that hosts use to modify a 17-kDa precursor (about 165 amino acids) ("DA17") of the protein. DA17 differs from DA15 in that DA17 has eight additional amino acids at the carboxy terminus. See B. Korant et al., 259 *J. Bio. Chem.* 14835–14839 (1984); D. Blomstrom et al., 261 *J. Bio. Chem.* 8811–8816 (1986); N. Reich et al., 84 P.N.A.S. USA 6394–6398 (1987); E. Knight et al., 263 *J. Bio. Chem.* 4520–4522 (1988). See N. Feltham et al., 9 *J. Interf. Res.* 493, 506 (1989). The art has to date been unable to determine the function of either DA15 or DA17.

Thus, it can be seen that a need exists for an improved means for stimulating a host defense mechanism by activating phagocytes.

SUMMARY OF THE INVENTION

We identify herein an effect of DA15 in the process of monocyte/macrophage activation. The latter cells, when activated, are essential components of the body's response to infections and cancer. In one embodiment, the present invention provides a process for stimulating a defense mechanism of a host. This involves the step of administering to the host a protein having substantially the structure of a protein selected from the group of DA15 and DA17, the protein having been produced outside of the host. The host (e.g. lymphocytes of the host) then produces interferon-gamma, which in turn stimulates the host defense activity of a phagocyte. In a preferred form, the exposing step takes place in the presence of lipopolysaccharide, the host is a mammal, and the phagocyte is either a monocyte or macrophage. In another preferred embodiment, the defense mechanism can be anti-tumor activity. Other possible defense mechanisms are activity against viruses, bacteria, rickettsia, or parasites, and/or enhancement of the monocyte structure.

In an alternative embodiment, there is provided a composition for stimulating a phagocyte, the phagocyte being of the type that normally takes part in a host defense mechanism of a mammal. There is provided an effective amount of a protein having substantially the structure of a protein selected from the group of DA15 and DA17, the protein having been produced outside the mammal whose defense mechanism is to be stimulated. There is also provided a carrier that does not exceed pharmaceutically acceptable toxicity to the mammal in the dosage that the composition delivers. In a preferred form, the phagocyte is selected from monocyte and macrophage, the carrier is a liquid (thus permitting injections), and the defense mechanism is anti-tumor activity.

It will be appreciated from the description above and the experiments described below that the inventors have discovered that a compound selected from the group of DA15 protein (and thus its precursor DA17 indirectly) stimulates macrophage and monocyte host defense mechanism activity, especially with respect to anti-tumor activity. This opens up important drug therapy uses for DA15 and DA17 (both in vitro and in vivo).

It is advantageous if proteins that activate monocytes and macrophages are exocellular proteins that initiate their biological activities by binding to a specific receptor on the exterior surface of mammalian cells. Unfortunately, proteins such as interleukin-1 remain cell associated. It has now been learned that DA15 /DA17 is released from the cell into the surrounding medium.

The objects of the invention therefore include:
(a) providing processes for stimulating host defense mechanism activity of macrophages and monocytes of the above kind; and
(b) providing compositions useful in connection with such processes.

These and still other objects and advantages of the present invention will be apparent from the description which follows. The following embodiments do not represent the full scope of the invention. Rather, the invention may be employed in other embodiments. Reference is therefore to be made to the claims herein for interpreting the scope of the present invention.

DESCRIPTION OF THE DRAWINGS

The controls (open boxes) in the figures 1-6 show that DA15 alone will not induce some of the defense mechanisms. For some defense mechanisms lipopolysaccharide (black boxes) is also needed. For others, LPS is not required.

BEST MODES FOR CARRYING OUT THE INVENTION

Preferred plasmids capable of expression DA15 and DA17 respectively have been deposited as ATCC 68216 on Feb. 8, 1990 (for DA15) and as ATCC 68236 on Feb. 21, 1990 (for DA17), both at the American Type Culture Collection, Rockville, Md., U.S.A., both under Budapest Treaty conditions. These cultures will be made available as required by applicable patent law. Such availability is not intended as a license. The DA15 strain is designated as *E. Coli* C-600, pBR322-TRP-IFN-15 kda. The DA17 strain is designated as *E. Coli* C-600, pBR322 TRP-IFN-17 kda. Both can be expressed using conventional techniques.

In the alternative, DA15 can be isolated from cells as described in D. Blomstrum, 261 *J. Biol. Chem.* 8811–8816 (1986) B. Korant et al., 259 *J. Biol. Chem.* 14835–14839 (1984); and N. Feltham et al., 9 *J. Interf. Res.* 493–507 (1989).

EXAMPLE I

Figure 1:
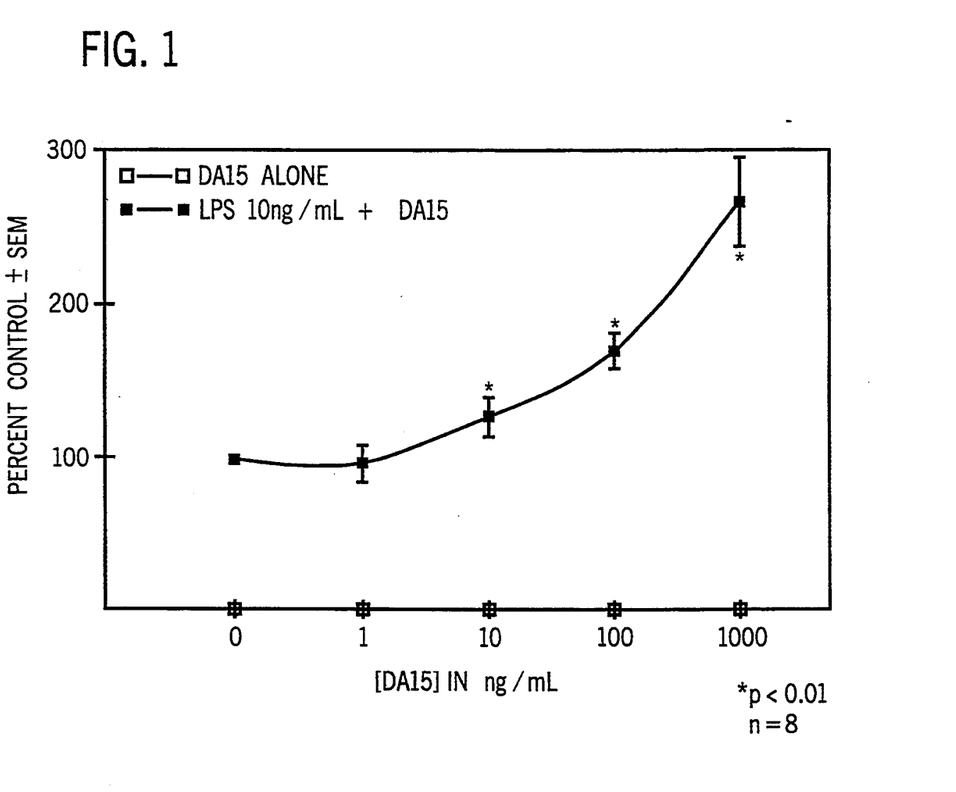
FIG. 1 depicts experiments evidencing activation of monocyte cytotoxicity by DA15. Without lipopolysaccharide ("LPS") no activation of this particular defense mechanism occurs with DA15. With LPS and DA15, activation increases with DA15.

To test the ability of DA15 to affect monocyte/macrophage activity, we chose as a first model system anti-tumor activity (see FIG. 1). We adapted a known $^{51}Cr$ cytotoxicity release assay for this purpose. In assays of this type, monocyte/macrophages can be pretreated with a test compound, and then compared with untreated monocyte/macrophages in their ability to lyse tumor cells that have been labelled with $^{51}Cr$. The higher the level of $^{51}Cr$ released, the more active the monocyte/macrophages. Techniques for $^{51}Cr$ release assays have been described in H. Ziegler-Heitbrock et al., 46 Can. Res. 5947–5952 (1986); H. Ziegler-Heitbrock et al., 72 JNCI 23–28 (1984); and R. Philip et al., 323 Nature 86–89 (1986), albeit not in connection with DA15.

Effector Cell Preparation

Monocytes ("effector cells") were derived from human peripheral blood. First fresh blood was drawn from healthy donors into tubes containing the anti-coagulant heparin (143 anti-coagulant units/10 mL). In an appropriately sized centrifuge tube, the whole blood is then layered on top of Ficol-Hypaque, a non-ionic polymer of sucrose, which is prepared to a specific density of 1.077 gm/mL. Since whole blood is less dense than the Ficol-Hypaque, it stays on top of the ficol. The ficol is warmed to 37° C. prior to use.

The tube containing the blood layered on top of the ficol is then spun in a centrifuge at 500×g for 30 minutes. All blood elements are then separated by density, with the heaviest elements being forced to the bottom of the tube. This causes all red cells to travel to the bottom of the tube, while monocytes remain suspended on top of the ficol layer. The polymorphonuclear cells (e.g. granulocytes and neutrophils) are in the lower portion of the tube along with the red cells. The plasma becomes the uppermost later because it is the least dense of all elements in the blood.

Once spun, the tube is gently removed from the centrifuge so as not to mix the plasma/ficol interface. The plasma is aspirated to within 1 cm of interface. The interface, containing the peripheral blood mononuclear cells ("PBM") is transferred, using a pasteur pipette to another tube for washing.

The new tube, containing the PBMs, is filled with Dulbecco's phosphate buffer saline solution (DPBS) (a solution of 0.9% NaCl buffered with phosphate buffers in order to keep the pH in the physiologic range). This salt solution is used to wash the cells. After the cells are resuspended, this tube is centrifuged for 15 minutes at 500×g. The supernatant is then aspirated and disposed of.

The effector cells are then resuspended in RPMI-1640 (a cell culture media), supplemented with 10% fetal bovine serum (FBS), 2 mM L-glutamine, and 50 μg/mL gentamicin (an antibiotic). The resuspended cells are again spun at 500×g for 8 minutes.

Supernatant is removed to the 1 mL mark on the centrifuge tube and the cells are counted using a hemocytometer. For the monocyte cytotoxicity assay, the working cell density (i.e. the number of PBMs per mL of media) is preferably $10^6$ cell/mL. A total of 1 mL of this cell suspension is made up for each subassay performed.

Target Cell Preparation

WEHI-164 is a murine cell line that was originally established from a fibrosarcoma induced by subcutaneous injection of 3-methylcholanthrene in BALB/c mice. See M. Rollinghoff et al., 144 Proc. Soc. Exp. Biol. Med. 813–818 (1973). The transplantable tumor was trypsinized in order to create a single cell suspension and recovered cells were propagated. This line is highly sensitive, after pretreatment with Actinomycin-D, to the effects of human cytotoxic monocytes, and thus provides a good target cell.

WEHI-164 can be grown in RPMI-1640 culture media supplemented with 10% FBS, 200 mM L-glutamine, and 50 μg/mL gentamicin. When grown in 25 $cm^2$ flasks in the upright position, they are loosely adherent (some cells stick to the plastic of the flask, others remain in suspension). The adherent cells can be dislodged by vigorous pipetting and then the cells can be kept in a logarithmic growth by constantly resupplying the cells with fresh supplemented media. This process is referred to as splitting the cells. The cells can be split at least 1:2 the day before use in an assay (1 mL of resuspended cells is added to 1 mL of fresh media) to achieve the best results.

10 mL of WEHI-164 cells can be spun down for 1 minute in a clinical centrifuge and 5 mL of the media can then be aspirated. 5 mL of Actinomycin-D at a concentration of 2 μg/mL can then be added to the WEHI-164 target cells, with the final Act-D concentration being 1 μg/mL. Cells can then be vortexed and incubated for 2 hours at 37° C. in 5% $CO_2$ and humidity. The cells are then vortexed every 30 minutes.

At the end of 2 hours of the Act-D treatment, the cells are washed three times in supplemented RPMI to remove any traces of the Act-D. Each wash consists of spinning the cells for 1 minute in the clinical centrifuge, aspirating media, and washing with 10 mL of supplemented RPMI.

To radiolabel the target cells, 50 μL of 5 mCi/mL $^{51}Cr$ is added to approximately 300 μL of media containing the WEHI-164 cell pellet for 90 minutes. The cells are incubated as above and vortexed every 30 minutes. At the end of the labelling incubation, the cells are washed three times with supplemented RPMI as above. Wash media is aspirated to the 1 mL mark on the centrifuge tube and a sample of the cells is counted in trypan blue at a 1:5 dilution.

Trypan blue is used to determine the viability of the cells prior to their use in the cytotoxicity assay. This is done because the Act-D pretreatment will adversely effect viability to some extent. When a cell is no longer viable, the membrane becomes permeable and trypan blue is able to enter it. If a cell stains blue with trypan blue, it is no longer viable. Cells that exclude the die are counted as viable.

Using this information, target cells are set to a concentration of 40,000 cells/mL in supplemented RPMI containing 40 ng/mL lipopolysaccharide. When 50 μL of cells are added to the assay, 2000 targets are added to each well. The final LPS concentration is 10 ng/mL.

Cytotoxicity Assay

Assays are preferably performed in a 96 well round bottom microtiter plate. Each microtiter plate is divided into quadrants. The divisions occur between D and E horizontally and 6 and 7 vertically. Therefore, each quadrant consists of 24 wells, 4 high by 6 wide.

100 μL of supplemented media is added to the first 5 columns of wells in each quadrant. 200 μL of monocyte effector cell suspension is then added to the sixth column in each quadrant. There are now 200,000 cells in the wells of the sixth column of each quadrant.

After vigorous pipetting, one transfers 100 μL of effector cell suspension from the sixth column of each quadrant to the fifth column (which has 100 μL media). Since 100,000 cells are being transferred, the final concentration of effector cells in the fifth column is 500,000/mL. The process is repeated with the fifth and fourth column (and then the other columns) so as to give progressive dilutions down to 37,250/ml.

In order to determine a maximum release standard of $^{51}Cr$ labelled target cells, samples of the cells are incubated in 150 μL of 3% Triton X-100. Triton X-100 is a non-polar detergent that causes 100% $^{51}Cr$ release by the cells.

Additional labelled tumor target cells are then mixed by inversion, and 50 μL of the target cell suspension (containing 10 ng/mL of LPS) is added to all wells. The monocytes and WEHI-164 cells are then incubated together for 6 hours at 37° in 5% $CO_2$ and humidity, and then harvested using a Titertek supernatant collection system.

It will be appreciated that the greater amount of radioactivity present in the supernate collected, the greater amount of lytic activity that is occurring, and therefore the greater amount of activity of the monocyte or macrophage. Thus, this assay provides a means for measuring the stimulation of the monocyte or macrophage.

DA15 Activation

When peripheral blood mononuclear cells are preincubated or primed with the DA15 protein for 2 hours prior to coming into contact with the WEHI-164 tumor targets, it was found that the cytotoxicity is markedly increased. See generally FIG. 1. Dosages have been found effective up to 3,000 ng/mL. The DA15 has lead to a significantly higher level of monocyte activity as measured by the assay.

As discussed in E. Knight et al., 263 *J. Bio. Chem.* 4520–4522 (1988), there is a 17 kDa precursor of DA15 ("DA17") that is about 165 amino acids and has a portion with substantially the same structure as DA15. It will be appreciated that instead of providing DA15, one could instead use the precursor in a cellular system providing the necessary COOH-terminal processing enzymes.

For use in the human body, it is expected that the preferred delivery will be an injection directly into the blood using a liquid carrier such as a buffered saline solution. Dosages will be set based on human tolerance and side effects, with likely maximum being levels equal 1000 ng/ml at the target cell site.

It is to be understood that the invention is meant to also include other variants, such as the use of solid carriers (tablet form). It is also to be expected that the DA15 might be linked to other compounds or modified slightly so as to cause the compound to be directed to particular areas of the body or to reduce side effects.

Further, it will be appreciated that the level of DA15 in the natural blood may be indicative of a disease state relative to monocytes. Thus, using the monocyte assay described herein in comparison with known DA15 standards, one can test for such levels. It should be noted that the term "substantially the structure" is to be interpreted as the compound plus its equivalents.

Figure 2:
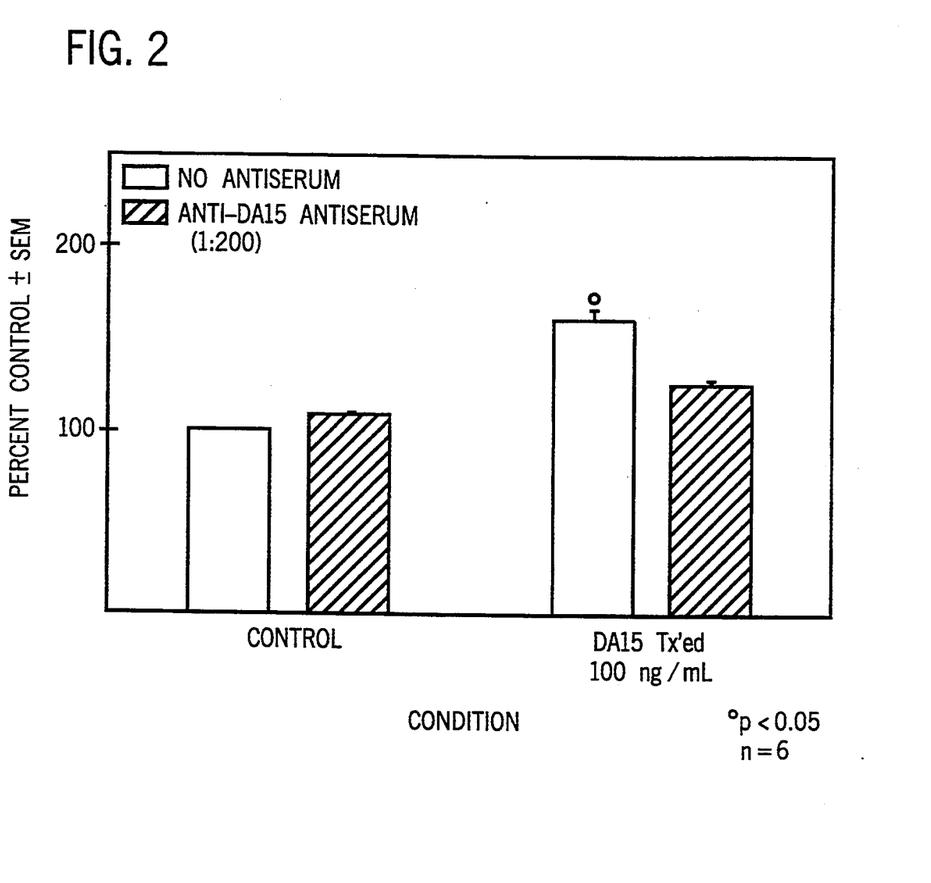
FIG. 2 confirms that blocking DA15 with an antiserum will block monocyte cytotoxicity.

As shown in FIG. 2, use of an anti-serum to DA15 blocks the activation effect of DA15.

Further Examples

As shown in FIGS. 3-6, other measures of monocyte activation were also examined (e.g. induction of TNF-alpha; IDO activity; IL-1 beta secretion; neopterin secretion) and these other tests also showed activation. Thus, DA15 (and DA17 indirectly) are involved in wide range of phagocyte activation.

Figure 3:
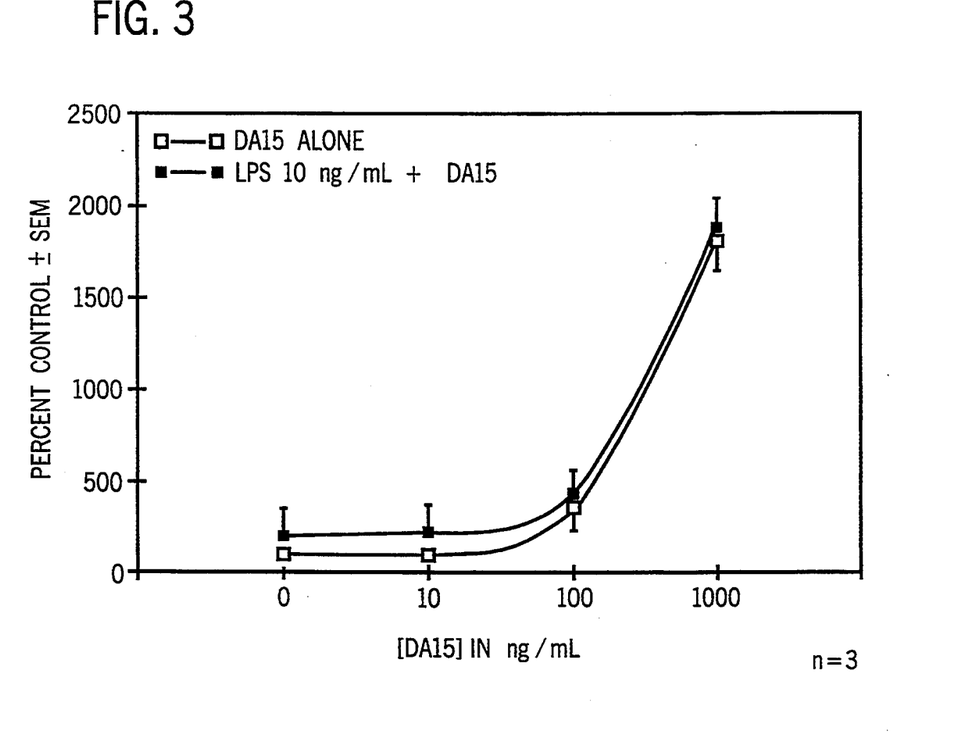
FIG. 3 evidences that DA15 induces tumor necrosis factor alpha, a compound known to mediate anti-tumor activity, with or without LPS.

TNF—Alpha—FIG. 3

In this regard, PEMs were derived as previously described for these otter measures of monocyte/macrophage activation. To measure tumor necrosis factor-alpha secreted into the media by PBMs treated for 24 hours with DA15, a commercially available ELISA was utilized (Endogen, Inc., Boston, Mass.). This ELISA is an in vitro enzyme-linked immunosorbent assay for the quantitative measurement of biologically active natural and recombinant TNF-alpha. It uses two distinct anti-TNF antibodies derived from two species, resulting in a test specific for human TNF-alpha. It is based on the dual antibody immunometric sandwich principle.

A polystyrene immunoplate is coated with mouse mono-clonal antibody specific for human TNF-alpha. The wells are then incubated with specimens and appropriate standards or controls. During this incubation, the TNF-alpha present in the test sample is captured and bound to solid phase. Unbound materials in the test sample are removed by aspiration and washing of the wells. Next the rabbit antibody to human TNF-alpha is added and incubated in the wells. This binds to TNF-alpha at multiple epitopes. Unbound second antibody is removed by aspiration and washing. A third enzyme-labeled goat anti-rabbit (conjugated with alkaline-phosphatase) is incubated in the wells. Unbound labeled antibody is removed by aspiration and washing. The bound specific anti-TNF-alpha antibody is quantitated by an enzymatic reaction resulting in a detectable color change using an ELISA reader. The measured absorbance (color change) is proportional to the concentration of the TNF-alpha in the test sample, within the working range of the assay. A standard curve is obtained by plotting the TNF-alpha concentration of the standards versus absorbance. The TNF-alpha concentration of the unknowns, run concurrently with the standards, are determined by comparison with the standard curve.

Figure 4:
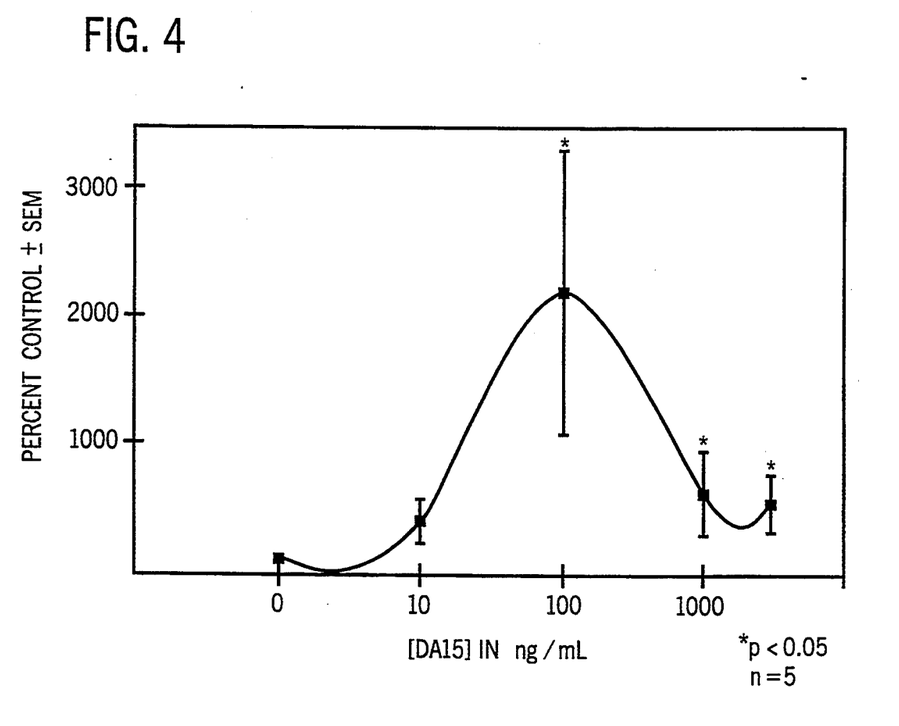
FIG. 4 evidences that DA15 induces indoleamine-2,3 dioxygenase activity, an anti-parasitic compound active in degrading trytophan.

IDO Activity—FIG. 4

Indoleamine-2,3-dioxygenase (IDO) activity is measured using a slight modification of a method described previously. See Y. Ozaki et al., 257 Arch. Biochem. Biophys. 207-216 (1987). The harvested PMB cell suspension is centrifuged at $250 \times g$ for 15 minutes with the resultant cell pellet lysed in 0.1 mL of 5 mM EDTA in 50 mM potassium phosphate buffer (KPB; pH 7.2) and centrifuged at $12,000 \times g$ for 15 minutes. Aliquots of 50 $\mu$L of this supernatant fraction were subjected to the Bradford protein assay (BIO-RAD, Richmond, Calif.) or IDO assay. The standard IDO assay mixture in a 1.5 mL microcentrifuge tube consists of 50 mM KPB, the cell lysate, 40 $\mu$M L-[ring-2-$^{14}$C]-tryptophan (1480 Bq; Research Product International Co.; Chicago, Ill.), catalase (4,200 units; Sigma), 10 mM sodium formate, oxygen at ambient tension (20.9%), 25 $\mu$M methylene blue, 10 mM ascorbic acid, and 5 mM EDTA in a total volume of 0.1 mL.

The reaction mixture is incubated at 37° C. for 30 minutes.

The reaction is terminated with the addition of 0.1 mL of 6% perchloric acid (PCA). Complete hydrolysis of [$^{14}$C]-formic acid from [$^{14}$C]-N-formylkynurenine is accomplished at 37° C. for 30 minutes. The labeled formate is separated from its precursors using the charcoal absorption method. One mL of 10% (w:v) charcoal-equilibrated with 1M formic acid in 3% PCA is added to the reaction mixture. The tubes are vortexed for 5 seconds and centrifuged at $3,000 \times g$ for 5 minutes. The supernatant is counted with a scintillation counter.

Figure 5:
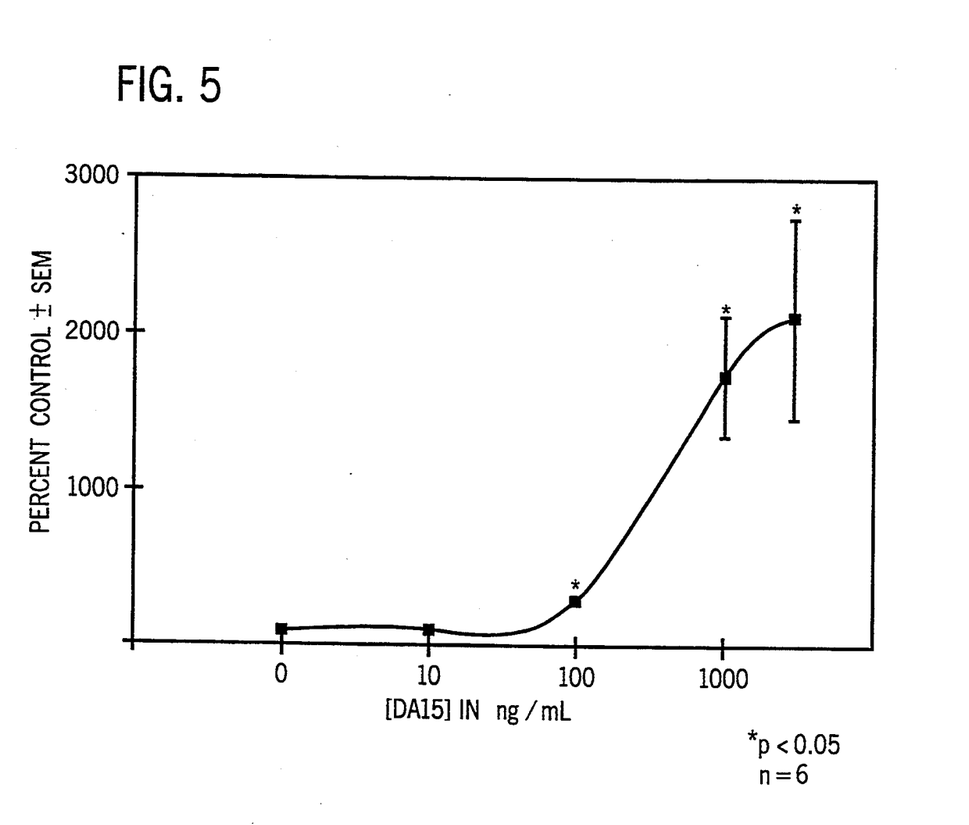
FIG. 5 evidences DA15 induction of interleukin-1 beta, a white cell related compound.

IL-1 Beta—FIG. 5

The IL-1$\beta$ secreted by PBMs incubated with DA15 is measured using an ELISA (Cistron Biotechnology, Pine Brook, N.J.) similar in principle to the TNF-alpha ELISA described above. In this system, a four-stage test is carried out in a microtitration well which has been coated with monoclonal antibody specific for IL-1$\beta$ (solid phase). In the first stage, a biological sample is added to a test well and incubated for a specified length of time. If IL-1$\beta$ is present in the sample, it will bind to the solid phase anti-IL-1 beta. If IL-1$\beta$ is not present, all sample components will be removed in the subsequent washing step. In the second stage, polyclonal rabbit anti-IL-$\beta$ is added to the test well. The antibody will bind specifically to solid phase bound IL-1$\beta$. If IL-1 beta is not present in the test sample, the unbound antibody will be removed in the subsequent washing step. In the third stage, goat anti-rabbit-IgG conjugated to horseradish peroxidase enzyme (conjugate) is added to the test well. The conjugate will bind specifically to solid phase bound rabbit IgG. If rabbit IgG is not present in the solid phase, the unbound conjugate will be removed in the subsequent washing step. In the fourth stage, the enzyme substrate is added to the test well. If bound conjugate is present, the substrate will be oxidized, resulting in a colored end product. Acid is added to stop the reaction and fix the color. The color intensity is proportional to the amount of bound conjugate and, therefore, to the amount of IL-1$\beta$ present in the biological sample. The color intensity is measured with a microtitration plate reader.

Figure 6:
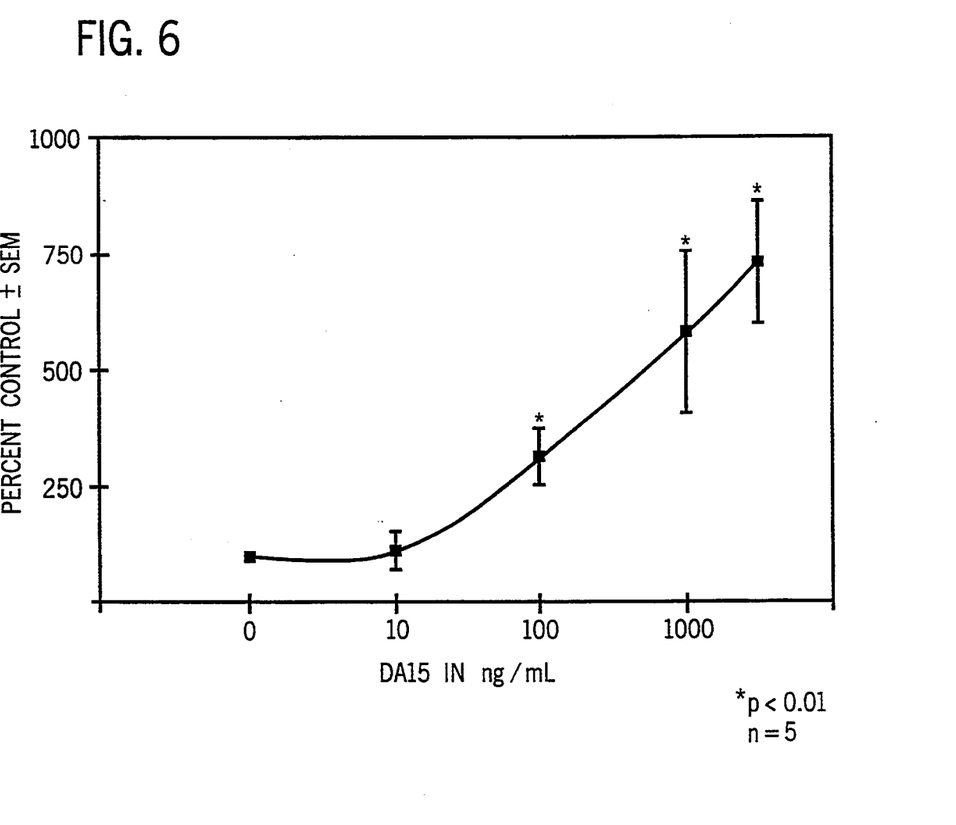
FIG. 6 evidences that DA15 induces neopterin.

Neopterin—FIG. 6

Neopterin measurement in the media of PBMs incubated with DA15 was performed by radioimmunoassay (Neopterin RIAcid, Henning, Berlin, FRG; distributed by DG International, Mountainside, N.J.). Media was stored at $-70°$ C. prior to assay. In this assay, anti-neopterin antibody which remains unbound after incubation with media complexes with a fixed amount of added $^{125}$I-labeled neopterin. The resulting antigen-antibody complexes are insolubilized by the addition of polyethylene glycol. An increasing concentration of unlabeled neopterin in the media of PBMs treated with DA15 results in smaller quantities of labeled antigen-antibody complexes, and thus lower radioactivity. All determinations are performed in duplicate with coefficients of variation less than 10%. The limits of detection with this assay are 1.25 to 160 nmol/L.

Interferon-gamma

Figure 9:
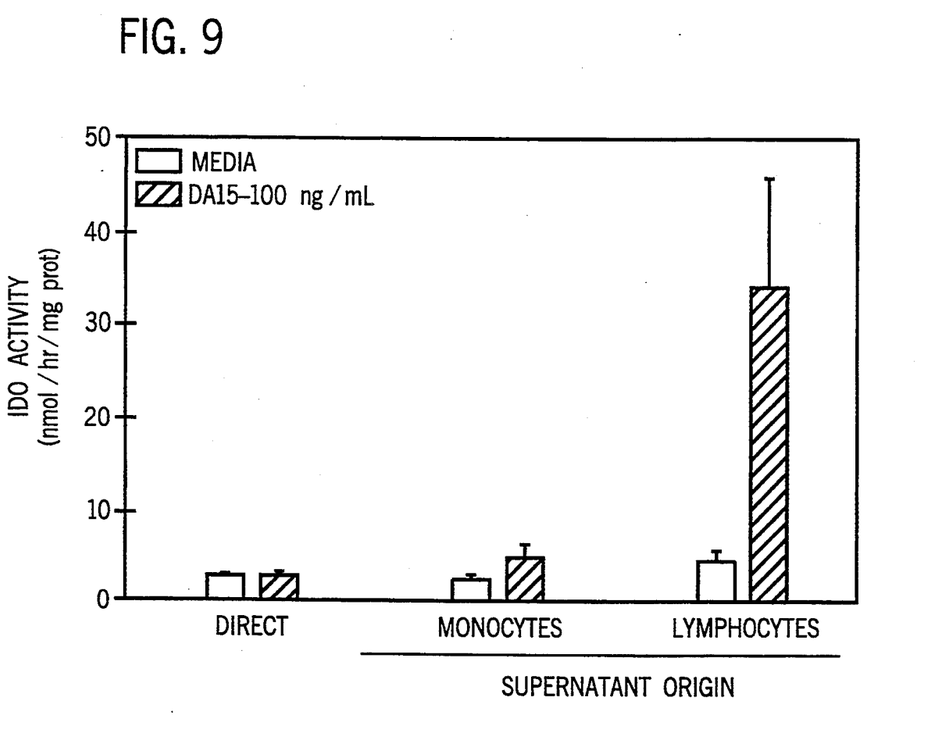
FIG. 9 evidences induction of IDO activity in 10 mM PMA pre-treated THP-1 cells by supernatants of lymphocytes (<85% T cell, <10% NK cells) treated with DA15. Media alone or DA15 alone had no effect on THP-1 cell IDO activity. Supernatants from monocytes (<85% monocytes) treated with either media alone or DA15 had no significant effect on IDO activity in THP-1 cells.

When populations of pure monocytes were incubated with DA15, no significant increase in monocyte cytotoxic activity was detected. This led us to examine the role of other secreted proteins in the PBM cultures incubated with the DA15. We found that DA15 treated supernatants from PBMs and pure lymphocytes had both antiviral and IDO inducing activity (FIG. 9). Both of these activities were in turn blocked by a polyclonal antibody directed against interferon-gamma. See R. Devos et al., 10 Nuc. Acids Res. 2488-2501 (1982) for a description of human interferon-gamma.

Figure 10:
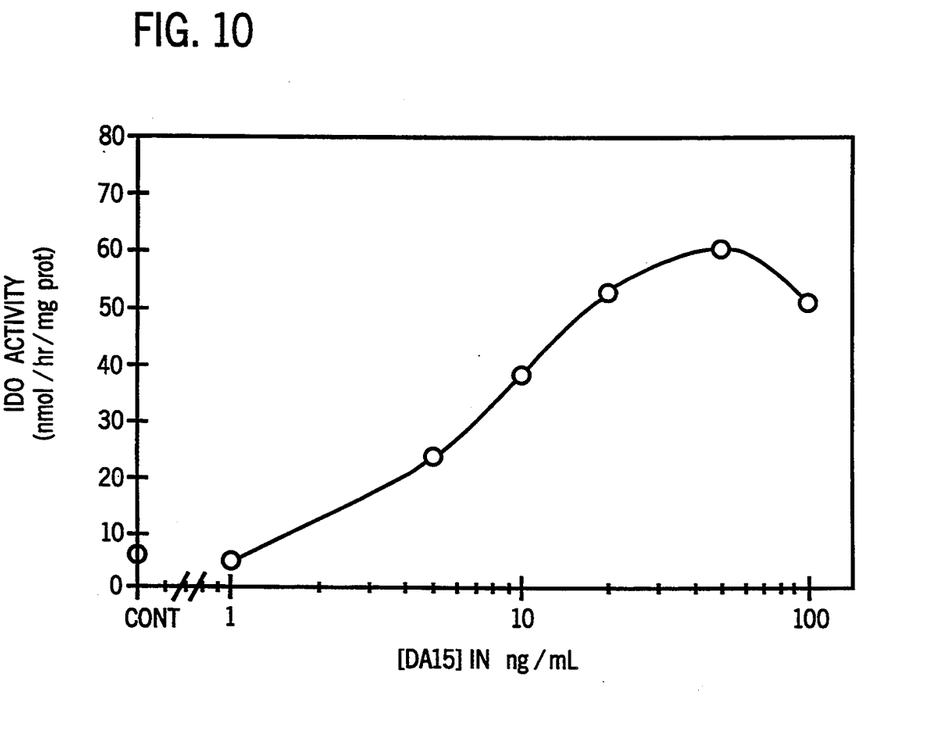
FIG. 10 evidences induction of IDO activity in pre-treated THP-1 cells by supernatants of lymphocytes treated with various concentrations ranging from 5 to 100 ng/ml of DA15.
Figure 11:
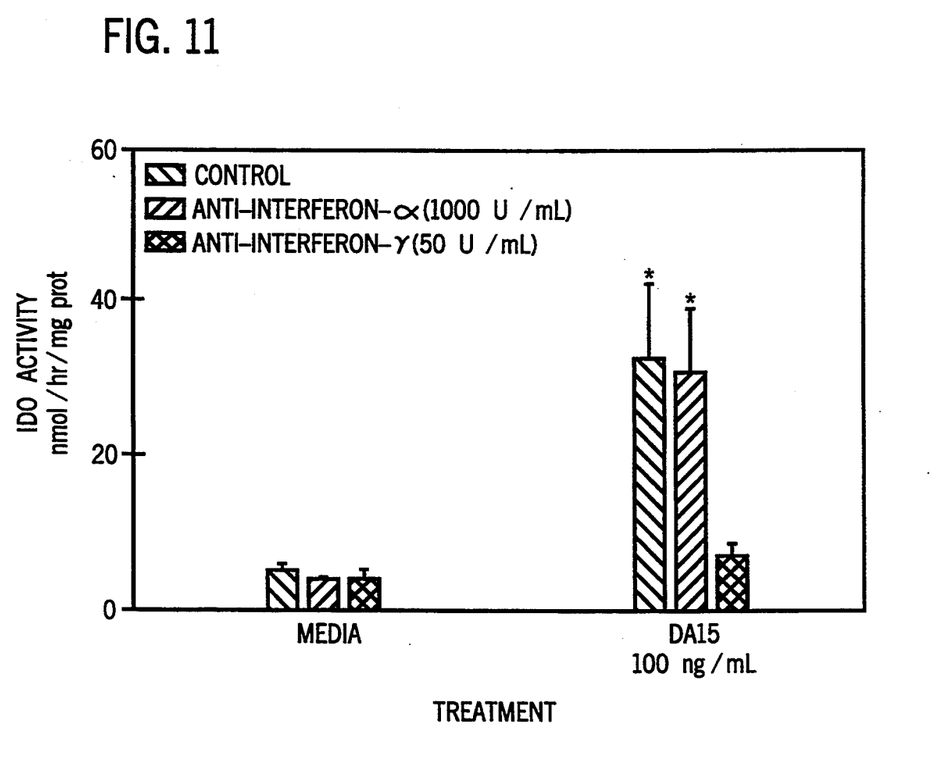
FIG. 11 evidences inhibition of the IDO induction by supernatants of lymphocytes cells treated with DA15 compared to cells also treated with antibodies to IFN β and gamma.
Figure 12:
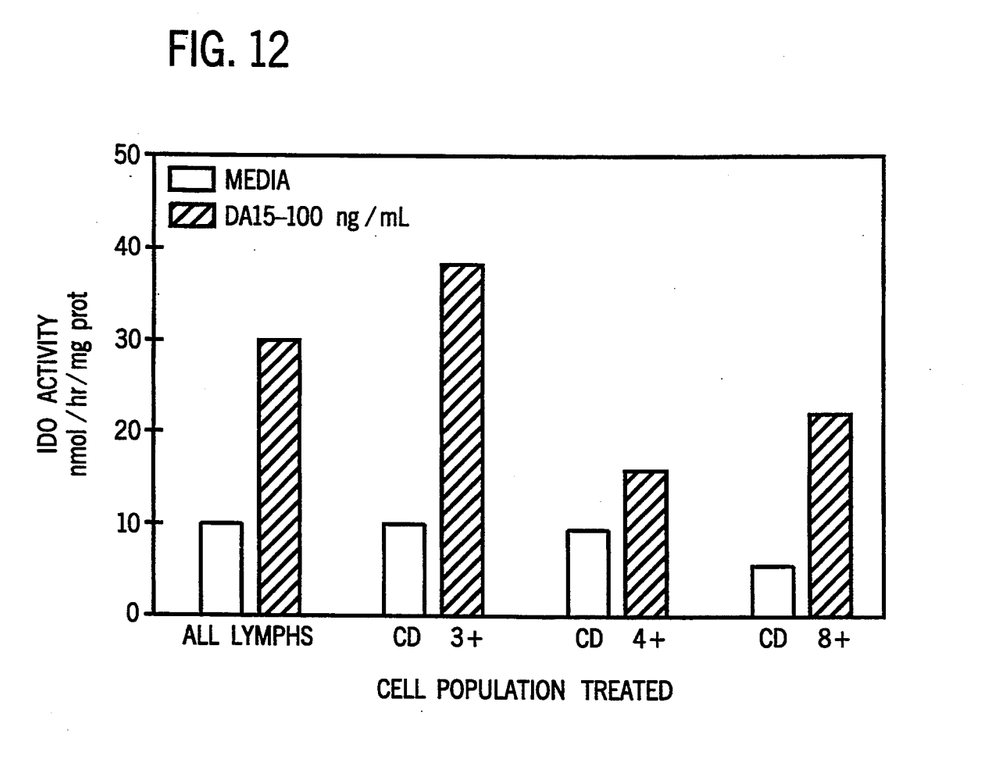
FIG. 12 evidences that various sub-populations of T-lymphocytes all produce IFN-gamma in response to DA15.

When PBMs were separated into two different populations, only T lymphocytes (NNA cells) were able to secrete a factor that had antiviral activity and caused THP-1 cells to induce (IDO) activity (FIGS. 9, 10). Monocytes, when treated with DA15, did not exhibit significant antiviral activity or cause THP-1 cells to induce significant IDO activity. Also, antibody directed against interferon-gamma, but not antibody directed against IFN-$\beta$, was able to inhibit the IDO inducing activity in supernatants from T cells treated with DA15 (FIG. 11).

IDO assay—IDO activity was measured using a slight modification of a method described in Y. Ozaki et al., 144 Biochem. Biophys. 1147 (1987). Treated cells were harvested and centrifuged at 250$\times$g for 15 minutes. The resultant cell pellet was lysed in 0.1 ml of 5 mM EDTA in 50 mM potassium phosphate buffer (KPB; pH 7.2) and centrifuged at 12,000$\times$g for 15 minutes. Aliquots of 50 $\mu$l of this supernatant fraction were subjected to the Bradford protein assay (GIO-RAD, Richmond, Calif.) or IDO assay.

The standard IDO assay mixture in a 1.5 ml microcentrifuge to be consisted of 50 mM KPB, the cell lysate, 40 $\mu$M L-[ring-2-$^{14}$C]-tryptophan (1480 Bq; Research Product International Co.; Chicago, Ill.), catalase (4,200 units: Sigma), 10 mM sodium formate, oxygen at ambient tension (20.9%), 25 $\mu$M methylene blue, 10 mM ascorbic acid, and 5 mM EDTA in a total volume of 0.1 ml. The reaction mixture was incubated at 37° C. for 60 minutes. The reaction was terminated with the addition of 0.1 ml of 6% perchloric acid (PCA).

Complete hydrolysis of [$^{14}$C]-formic acid from [$^{14}$-C]-N-formylkynurenine was accomplished at 37° C. for 30 minutes. The labeled formate was separated from its precursors using the charcoal absorption method. One ml of 10% (w:v) charcoal-equilibrated with 1M formic acid in 3% PCA was added to the reaction mixture. The tubes were vortexed for 5 seconds and centrifuged at 3,000$\times$g for 5 minutes. The supernatant was counted with a scintillation counter.

Interferon-gamma production—PBMs were isolated as previously described. In order to deplete the PBM population of those cells known not to produce IFN-gamma, a 60 minute nylon wool adherence was carried out as described in M. Julius et al., 3 Eur. J. Immunol. 645 (1973). This procedure rids a population of PBMs of both monocytes and B cells. Freshly isolated PBMs were concentrated to a total of 2 ml. These were incubated over a nylon wool column at 37° C. in 5% $CO_2$ for 60 minutes. Nylon nonadherent (NNA) cells (B cell depleted lymphocytes) were extensively washed with cRPMI (RPMI-1640 containing 28.8 mM $NaHCO_3$ and 27.8 mM HEPES supplemented with 10% fetal bovine serum, 2 mM L-glutamine, and 50 $\mu$g/ml gentamicin). Phenotypically, they were >85% CD-3+ and >10% CD-16+ (markers of T cells and NK cells, respectively), while being <2% CD-16+ and <2% CD-19+ (markers of monocytes and B cells, respectively) by FACS analysis (Becton Dickinson). Alternatively, pure lymphocytes were obtained by elutriatioin of normal donors. The NNA cells, at a concentration of 10$\times$10$^6$ml, were treated with varying doses of DA15 for 1-3 days. Supernatants were collected and used iin antiviral and IFN-gamma bioassay.

Antiviral assay—Interferon-gamma antiviral activity was determined in a conventional cytophathic effect (CPE) inhibition assay of vesicular stomatitis virus (VSV) on human anion (WISH) cells. WISH cells were seeded into 96-well microtiter plates (CoStar) in a volume of 100 $\mu$l/well. To this was added 50 $\mu$l of serially diluted test supernatants. Twenty-four hours later, 50 $\mu$l of 200 $TCID_{50}$ VSV was added to each well. Fortheight hours post-infection, the tissue monolayer was scored visually for virus-induced CPE. The IFN titer was defined as the reciprocal of the highest dilution showing at least 50% inhibition of CPE in triplicate culture.

IFN-gamma bioassay-THP-1 (ATCC) cells pretreated with 10 nM PMA (Sigma) have been shown to be sensitive to the IDO inducing effects of IFN-gamma in M. Edelstein et al., 143 J. Immunol. 2969 (1989). PMA alone has no effect on IDO activity in these cells. When the cells were treated with DA15 alone, IDO activity was not enhanced. This model system was used to test the bioactivity of the IFN secreted by NNA cells treated with DA15. PMA pre-treated THP-1 cells were washed and incubated with supernatants from DA15 treated NNA cells. IDO activity was assessed after 24 hours of incubation. A standard IFN-gamma curve was run in parallel in order to assess the amount of secreted IFN-gamma present in the supernatants.

Neutralizing antibodies—Antibody directed against purified, natural DA15 produced in IFN-$\beta$ treated Daudi cells was used at a dilution of 1:200 for DA15 blocking experiments. The antibody was produced in rabbits. Anti-IFN-gamma neutralizing antibody (Genzyme) was used at a concentration of 50 NU/ml. Anti-IFN-$\alpha$ neutrallizing antibody (Berrhinger Mannheim) was used at a concentration of 500 NU/ml.

Results—Indoleamine 2,3-dioxygenase (IDO), a heme-containing enzyme that catalyzes the pyrrole ring oxidative cleavage in the degradation of L-tryptophan to L-N-forymlkynurenine, has been shown to be induced by interferon-gamma in a variety of human and animal tissues. The induction of this enzyme has been shown to result in the inhibition of bacterial and protozian intracellular pathogens, and therefore appears to play a role in host response to microbial infections. J. Carlin et al., 9 J. Inter. REs. 329 (1989).

Figure 7:
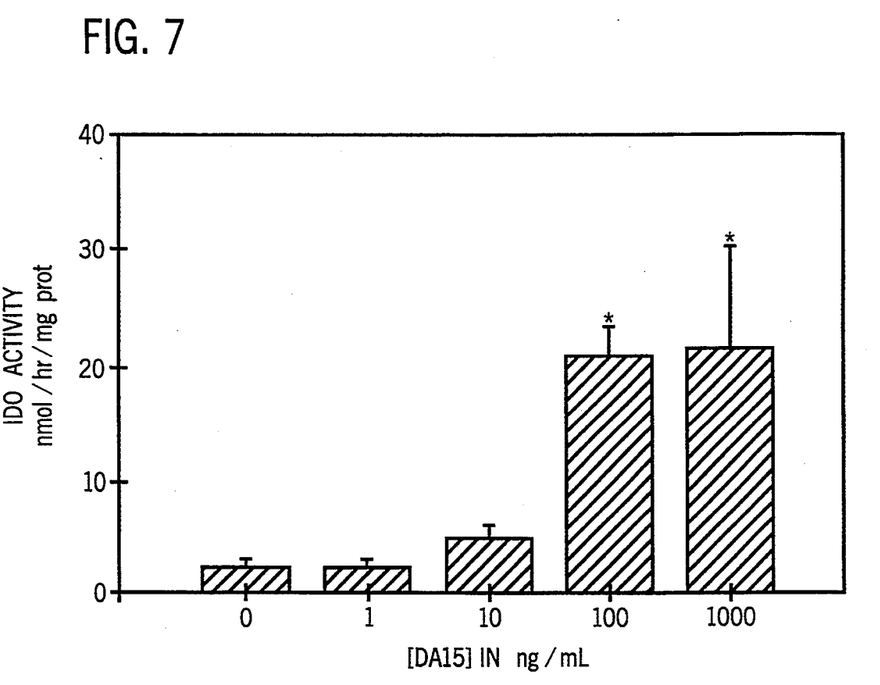
FIG. 7 confirms induction of indoleamine 2,3-dioxygenase ("IDO") activity in peripheral blood mononuclear cells (PBM's) treated with DA15 for 72 hours.
Figure 8:
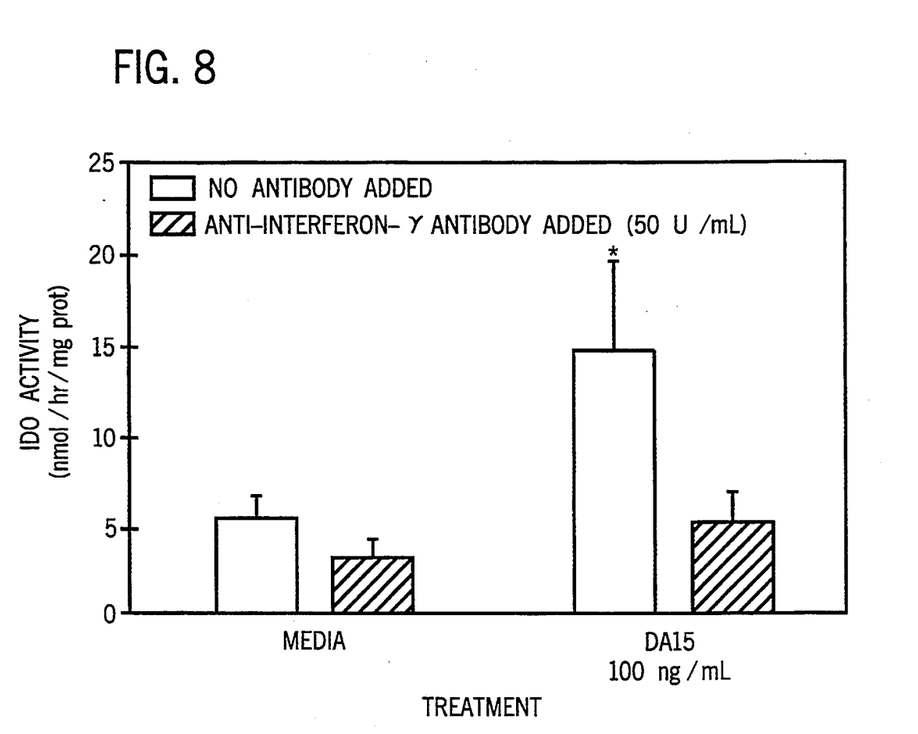
FIG. 8 evidences inhibition of DA15 induced IDO activity in PBMs by the addition of interferon-gamma neutralizing antibody. The empty box indicates no antibody added. Antibody was added concurrent to the addition of DA15 during the 72 hours of incubation of PBMs.

When PBMs were stimulated with DA15 for 72 hours, at a variety of concentrations, IDO activity was increased in a dose responsive manner (FIG. 7). Antiserum to DA15 was able to block DA15 induced IDO activity, as was heating of the DA15 prior to its addition to the PBMs. When polyclonal antibody directed against IFN-gamma was added to the system, DA15 induction of IDO activity was also reversed (FIG. 8). This indicates that the DA15 does not act directly on the monocytes. Rather, it acts via the secretion of IFN-gamma, which in turn then acts to induce monocyte activation. This also explains the fact that DA15 is unable to potentiate monocyte cytotoxicity in pure preparations of monocytes.

Note that when lymphocytes were treated with DA15 and the supernatants were tested for antiviral activity, antiviral activity was induced by DA15. Supernatants from DA15 treated lymphocytes exhibited antiviral activity whereas none was present in lymphocytes treated with media alone. Antibody neutralization studies indicated that DA15 acts through IFN-gamma.

TABLE 1

PRODUCTION OF IFN-γ IN HUMAN LYMPHOCYTES TREATED WITH RECOMBINANT OR NATURAL DA15
(as measured by antiviral activity)

| type | preparation | concentration | IFN-γ produced (antiviral units) |
| --- | --- | --- | --- |
| recombinant | 1 | 100 ng/ml | 16 U/ml |
| recombinant | 1 | 200 ng/ml | 32 U/ml |
| recombinant | 2 | 200 ng/ml | 256 U/ml |
| recombinant | 3 | 100 ng/ml | 1280 U/ml |
| recombinant | 4 | 100 ng/ml | 320 U/ml |
| recombinant | 5 | 100 ng/ml | 640 U/ml |
| natural | 6 | 100 ng/ml | 80 U/ml |

Note that it was recently reported that IFN-gamma was able to greatly induce IDO activity in THP-1 human monocytoid cells after treatment with PMA, although PMA alone had no effect on IDO activity. See M. Edelstein et al., 143 J. Immunol. 2969 (1989). In our experiments, PMA pre-treated THP-1 cells were incubated for 24 hours with DA15 induced IFN-gamma containing supernatants (FIG. 9). The DA15 alone had no effect on IDO activity in THP-1 cells. However, supernatants from lymphocytes (>85% CD-30, >8% CD-16+) treated with DA15 at concentrations ranging from 5 to 100 ng/ml greatly induced IDO activity. Supernatants from lymphocytes treated with cRPMI alone did not induce IDO activity. Supernatants from monocytes (>85% CD-14+) treated with DA15 did not induce IDO activity in the PMA pre-treated THP-1 cells.

Discussion

Interferon-induced DA15 protein is slowly released by human monocytes into the exocellular medium after the induction of its synthesis by interferon. In this regard, human monocytes in cell culture were treated with human interferon alpha, beta, or gamma, and the quantity of intracellular and exocellular 15-kDa protein was determined at various times after the start of its synthesis. At least 50% of the total DA15 protein can be found in the exocellular medium twenty four hours after its intracellular synthesis. The exocellular role appears to be cell-to-cell signaling in that DA15 activates a blood cell such as a monocyte, thereby inducing a biological response in the blood cell. Further, in accordance with the present invention it has been learned that this signaling leads to monocyte activation.

We claim:

1. A method of producing interferon-gamma in mammalian CD3+ T-cells, comprising the step of:

administering to mammalian CD3+ T-cells an effective amount of a protein having the structure of DA15 so as to expose at least some of the CD3+ T-cells to a concentration of the protein that can induce interferon-gamma production in CD3+ T-cells, said concentration being between 10 and 1000 ng/mL, the protein having been produced outside the host;

whereby the CD3+ T-cells produce interferon-gamma, and wherein said administering is in vitro.

* * * * *